United States Patent [19]

Clifford

[11] 4,040,428
[45] Aug. 9, 1977

[54] CONTROL VALVES FOR TRACHEOTOMY PATIENT OR LARYNGEAL PROSTHESIS

[75] Inventor: Earl W. Clifford, Getzville, N.Y.

[73] Assignee: The Aro Corporation, Bryan, Ohio

[21] Appl. No.: 718,946

[22] Filed: Aug. 30, 1976

[51] Int. Cl.² .................. A61M 25/00; A61F 1/20; A61M 16/00
[52] U.S. Cl. .................. 128/351; 3/1.3; 137/521
[58] Field of Search ............ 3/1.3; 128/351, 145 A

[56] References Cited

U.S. PATENT DOCUMENTS

| | | | |
|---|---|---|---|
| 2,804,076 | 8/1957 | Giraudon | 3/1.3 UX |
| 3,747,127 | 7/1973 | Taub | 3/1.3 |
| 3,844,290 | 10/1974 | Birch et al. | 128/351 |
| 3,952,335 | 4/1976 | Sorce et al. | 3/1.3 |

FOREIGN PATENT DOCUMENTS

| | | | |
|---|---|---|---|
| 2,262,508 | 9/1975 | France | 3/1.3 |

*Primary Examiner*—Ronald L. Frinks
*Attorney, Agent, or Firm*—Sommer & Sommer

[57] ABSTRACT

The present invention provides improvements in a control valve adapted to be used by a tracheotomy patient or in a laryngeal prosthesis. In one form, the control valve has a housing provided with a control opening, and a flapper mounted within the housing and operable to move toward and away from the control opening. In this form, the improvement includes a thumbscrew mounted to penetrate the housing to engage the flapper, such that the thumbscrew may be selectively rotated to vary the operational characteristics of the valve. In another form, particularly adapted to be used by a tracheotomy patient, the control valve is provided with a first control opening communicating with ambient atmosphere and a second control opening adapted to communicate with the trachea of a patient. In this form, the flapper is operatively mounted within the housing and is adapted to selectively close or pass through these control openings to enable the patient to normally inhale or exhale through his mouth or nose, but to enable the patient to cough or gasp for air directly through the control valve.

3 Claims, 10 Drawing Figures

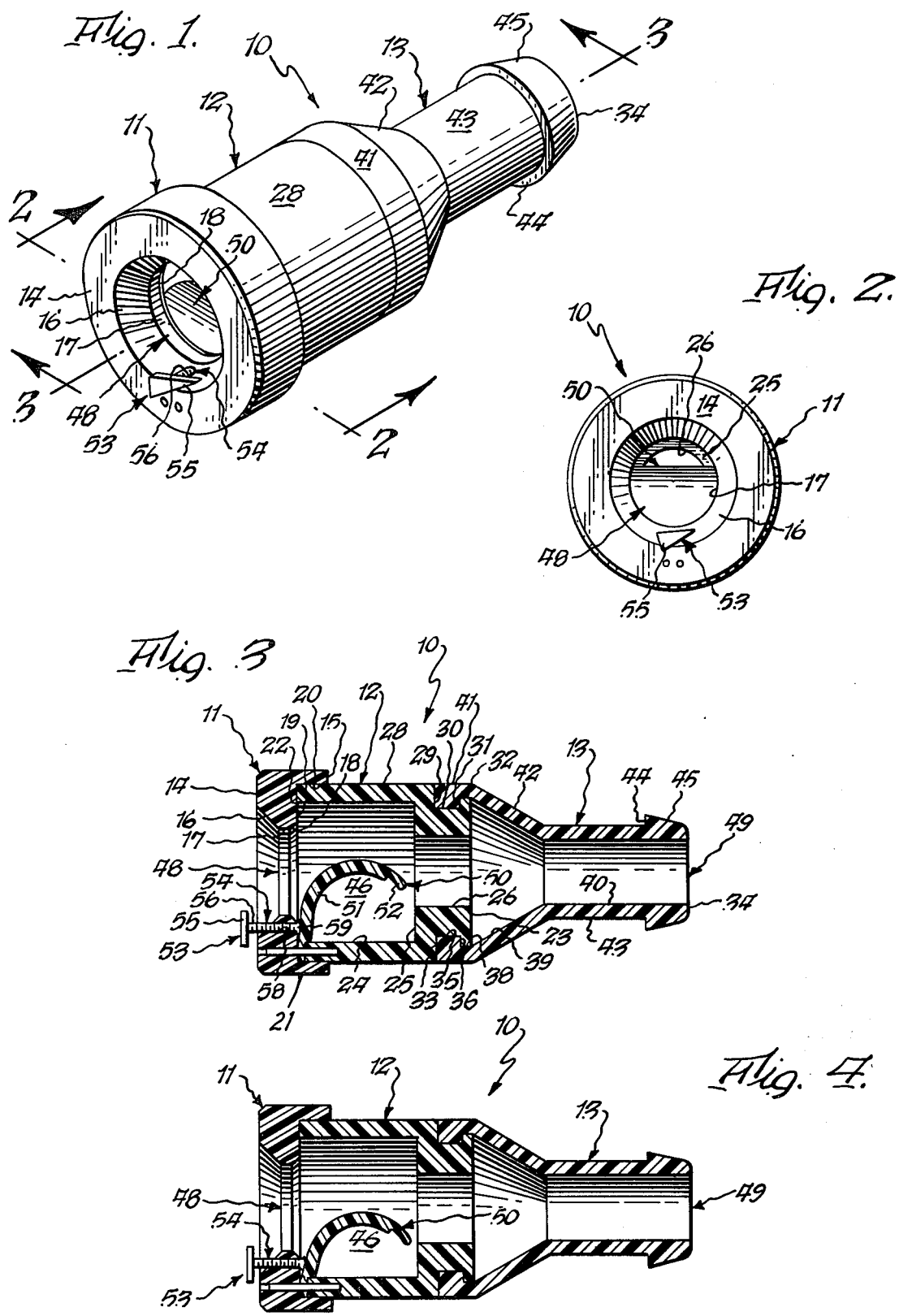

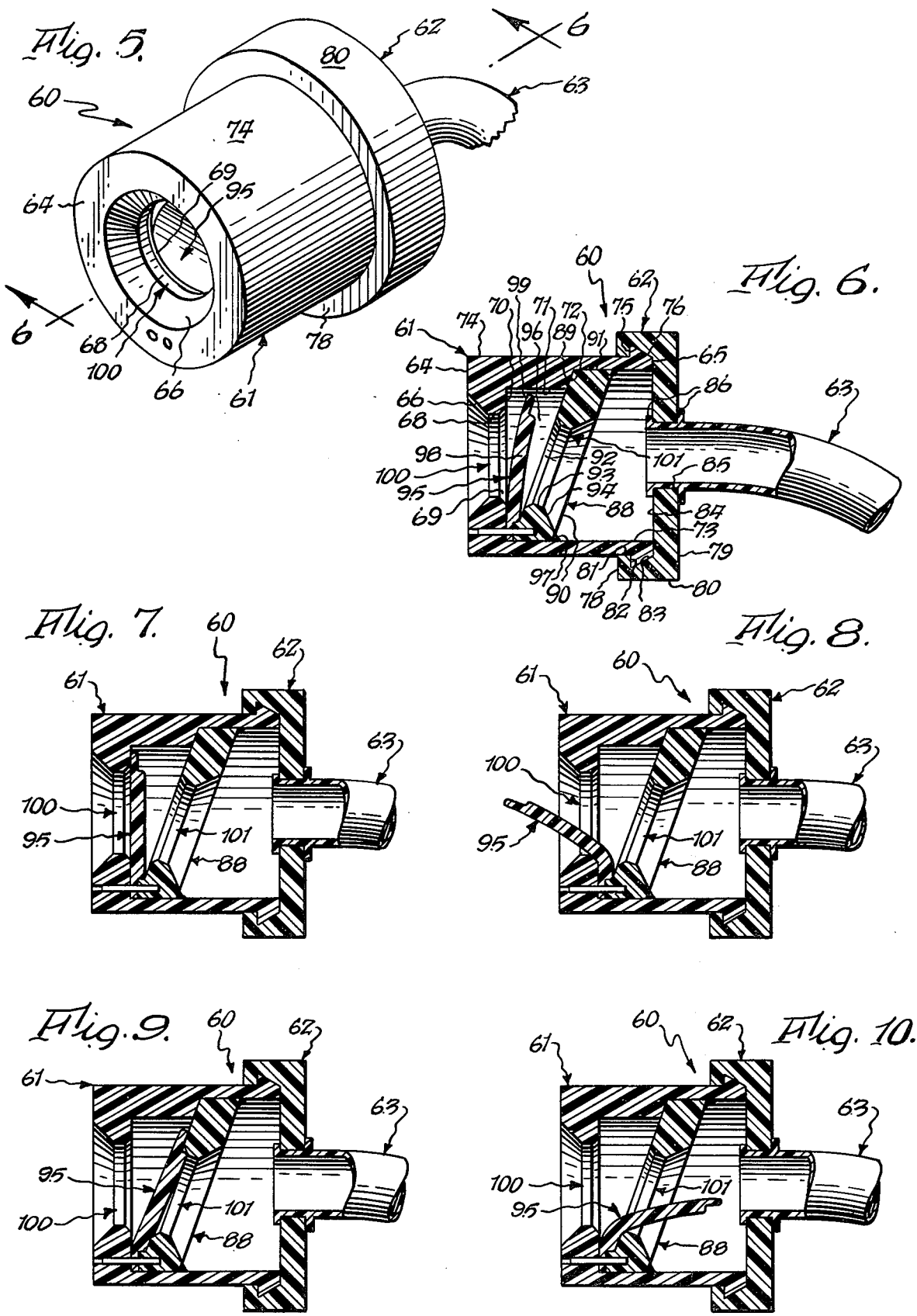

CONTROL VALVES FOR TRACHEOTOMY PATIENT OR LARYNGEAL PROSTHESIS

BACKGROUND OF THE INVENTION

1. Field of the Invention

The present invention relates generally to the field of control valves for use in a laryngeal prosthesis, or for use in rehabilitating a tracheotomy patient.

2. Description of the Prior Art

The present invention discloses and claims two forms of improved control valves of the type disclosed in U.S. Pat. No. 3,952,335, entitled "Laryngeal Prosthesis," the aggregate disclosure of which is hereby incorporated by reference to amplify the description of structure and operation of the inventive control valves herein disclosed and claimed.

The said U.S. Pat. No. 3,952,335 discloses a unique control valve having a housing defining a chamber therewithin, a tracheal opening adapted to communicate this chamber with the patient's trachea, and a control opening communicating the chamber with ambient atmosphere. A flapper is mounted on the housing within the chamber, and is adapted to move toward and away from the control opening to enable the patient to inhale and exhale through the valve at normal levels, but to pass through the control opening should the patient cough.

However, while the structure disclosed in said patent is believed to be completely satisfactory, it has been realized that a patient's breathing levels may vary as a function of physical activity or exertion. The structure disclosed in said patent does not provide means for adjusting the operational characteristics of the valve to accommodate for different breathing levels of the same patient.

Also, it has been found that the structure disclosed in said patent may be uniquely modified to provide an improved control valve which is adapted to be used to rehabilitate a tracheotomy patient. As persons skilled in this art will realize, a tracheotomy patient is normally provided with a tracheal fistula or stoma through which the patient may breathe. However, when such patient desires to breathe normally through his mouth or nose, he must first cover his tracheal opening. Upon information and belief, tracheotomy patients are normally provided with a "Jackson tube," a "Shiley tube," or equivalent, and common practice has been to simply block such passage through use of a simple cork or other suitable closure device. While this expedient may appear to be adequate, its drawbacks far outweigh its advantages. Should the patient be unable to breathe through his nose or mouth, and gasp for air, the cork will block the tracheal opening. Hence, the cork-expedient, which is understood to be in common practice in hospitals today, requires that the patient or an attendant physically remove the cork or plug to clear the tracheal airway.

SUMMARY OF THE INVENTION

The present invention overcomes the deficiencies noted in the prior art by providing an improved control valve for use in a laryngeal prosthesis or by a tracheotomy patient. Moreover, the present invention discloses and claims specific improvements to the structure disclosed in U.S. Pat. No. 3,952,335.

In one form, such an improved control valve may have a housing defining a chamber therewithin, and a flapper mounted on the housing in the chamber. The housing has a control opening communicating the chamber with ambient atmosphere. The flapper is adapted to move from a normal position toward and away from the control opening. In this form, the improvement broadly comprises adjustment means mounted on the housing and adapted to engage the flapper for enabling the normal position of the flapper to be selectively moved away from the control opening, whereby the operational characteristics of the control valve may be selectively varied. In this manner, the control valve may be selectively adjusted to accommodate different breathing levels of the wearer.

In one preferred embodiment of this improved control valve, the adjusting means may simply include a thumbscrew operatively arranged to penetrate the housing to engage the flapper such that the thumbscrew may be selectively rotated to move the normal position of the flapper further away from the control opening.

In another aspect, the present invention provides a unique control valve for use by a tracheotomy patient provided with a tracheal fistula, and adapted to require the patient to breathe normally through his mouth, but adapted to enable the patient to breathe heavily through the tracheal fistula. This improved control valve may comprise a housing defining a chamber therewithin, and a flapper mounted on the housing in the chamber. The housing is provided with a first control opening communicating the chamber with ambient atmosphere, and provided with a second control opening adapted to communicate the chamber with the tracheal fistula. A marginal portion of the housing about each of the control openings defines a seat facing the other of the control openings. The flapper is mounted on the housing in the chamber for movement between the two control openings, and has a flexible peripheral marginal portion. The flapper is adapted to move toward and sealingly assume the contour of the seat about the first control opening to close the first control opening when the patient normally exhales, and is also adapted to move toward and sealingly assume the contour of the seat about the second control opening to close the second control opening when the patient normally inhales. In this manner, the patient is forced to breathe normally through his mouth. In this control valve, the flapper is adapted to pass through the first control opening, by deformation of the flapper marginal portion, should the patient cough. Conversely, the flapper is adapted to pass through the second control opening, again by deformation of the flapper marginal portion, should the patient gasp for air.

Accordingly, one general object of the present invention is to provide an improved conrol valve.

Another object is to provide an improved control valve for use in a laryngeal prosthesis or by a tracheotomy patient, which enables the wearer to adjust the operational characteristics of the valve to accommodate different breathing levels of the patient.

Another object is to provide an improved control valve for a tracheotomy patient, which effectively forces the patient to breathe normally through his nose and mouth, but automatically enables the patient to cough or gasp for air through his tracheal fistula.

These and other objects and advantages will become apparent from the foregoing and ongoing specification, the drawings, and the appended claims.

BRIEF DESCRIPTION OF THE DRAWINGS

FIG. 1 is a perspective exterior view of an improved control valve incorporating the inventive adjusting means.

FIG. 2 is an end elevation of the control valve, taken generally on line 2—2 of FIG. 1, showing the thumbscrew.

FIG. 3 is a longitudinal vertical sectional view of the improved control valve, taken generally on line 3—3 of FIG. 1, showing the thumbscrew penetrating the housing to engage the flapper.

FIG. 4 is a view generally similar to FIG. 3, but showing the thumbscrew as having been suitably rotated to move the normal position of the flapper further away from the control opening to vary the operational characteristics of the control valve.

FIG. 5 is a perspective exterior view of an improved control valve for a tracheotomy patient.

FIG. 6 is a longitudinal vertical sectional view thereof, taken generally on line 6—6 of FIG. 5, this view particularly showing the housing, the chamber, and the flapper mounted for movement between the first and second control openings.

FIG. 7 is a fragmentary view of the control valve depicted in FIG. 6, but showing the flapper as having been moved to close the first control opening when the patient normally exhales.

FIG. 8 is a fragmentary view of the control valve depicted in FIG. 6, but showing the flapper as having passed through the first control opening when the patient coughs or exhales heavily to relieve an undesirable back pressure.

FIG. 9 is a fragmentary view of the control valve depicted in FIG. 6, but showing the flapper as having moved to close the second control opening when the patient normally inhales.

FIG. 10 is a fragmentary view of the control valve depicted in FIG. 6, but showing the flapper as having passed through the second control opening when the patient gasps for air.

DESCRIPTION OF THE PREFERRED EMBODIMENTS

At the outset, it should be clearly understood that like reference numerals are intended to identify the same elements and/or structure consistently throughout the several drawing figures, as such elements and/or structure may be further described or explained by the entire written specification of which this detailed description is an integral part.

First Preferred Embodiment (FIGS. 1-4)

Referring collectively to FIGS. 1-4, a control valve of the type disclosed in U.S. Pat. No. 3,952,335, is generally indicated at 10. This control valve 10 is shown as including a housing having, from left to right in FIG. 1, a leftward end cap 11, a tubular intermediate part 12, and a horizontally elongated tubular right part 13.

As best shown in FIG. 3, the housing end cap 11 has an annular vertical left end face 14; an annular vertical right end face 15; an inner surface sequentially including, from left to right in FIG. 3, a rightwardly convergent frusto-conical inclined surface 16 extending rightwardly from end face 14, a horizontal cylindrical surface 17, a rightwardly divergent frusto-conical seat surface 18, an annular vertical surface 19, and a horizontal cylindrical surface 20 extending rightwardly therefrom to join right end face 15; and a horizontal cylindrical outer surface 21 joining the two end faces.

The housing tubular intermediate part 12 is shown as including an annular vertical left end face 22; an annular vertical right end face 23; an inner surface including, from left to right in FIG. 3, a horizontal cylindrical surface 24 extending rightwardly from left end face 22, a leftwardly facing annular vertical surface 25, and a horizontal cylindrical surface 26 extending rightwardly to join right end face 23; and an outer surface including, from left to right in FIG. 3, a horizontal cylindrical surface 28 extending rightwardly from left end face 22, a rightwardly facing annular vertical surface 29, a horizontal cylindrical surface 30, a leftwardly facing annular vertical surface 31, and a horizontal cylindrical surface 32 continuing rightwardly to join right end face 23. Thus, surfaces 29, 30 and 31 define an annular trough or groove about the right end of the intermediate part 12 to capture the left marginal end portion of the tubular right part 13.

The housing tubular right part 13 is shown as including an annular vertical left end surface 33; an annular vertical right end surface 34; an inner surface including, from left to right in FIG. 3, a horizontal cylindrical surface 35 extending rightwardly from left end face surface 33, a rightwardly facing annular vertical surface 36, a horizontal cylindrical surface 38, a rightwardly convergent frusto-conical surface 39, and a horizontal cylindrical surface 40 continuing rightwardly therefrom to join right end face 34; and an outer surface including, from left to right in FIG. 3, a horizontal cylindrical surface 41 extending rightwardly from left end face 33, a rightwardly convergent frusto-conical surface 42, a horizontal cylindrical surface 43, a leftwardly facing annular vertical surface 44, and a rightwardly convergent frusto-conical surface 45 continuing rightwardly to join right end face 34. Thus, the left marginal end portion of tubular part 13 is provided with an inwardly directed lug which is adapted to be received in the cooperative groove provided in the right marginal end portion of intermediate part 12.

The control valve 10 thus includes a housing formed by assembling housing left end cap 11, housing intermediate part 12, and housing right part 12 together in the manner shown in the drawings, this housing defining a chamber 46 therewithin and provided with a leftward control opening, generally indicated at 48, communicating the chamber with ambient atmosphere, and provided with a rightward tracheal opening, generally indicated at 49, adapted to communicate chamber 46 with a patient's tracheal fistula.

Still referring principally to FIG. 3, the control valve is shown as further including a flapper, generally indicated at 50, mounted on the housing in the chamber, and adapted to move toward and away from control opening 48 to enable the patient to inhale, exhale and cough therethrough.

As more fully described in U.S. Pat. No. b 3,952,335, the entire disclosure of which is herein incorporated by reference, the flapper 50 is shown as being a normally arcuate member having a central spring portion 51, and an outer flexible marginal portion 52 which is adapted to deform to enable the flapper to pass through the control opening 48 should the patient cough. This flapper 50 is preferably formed of silicone, or some other suitable material. The spring portion 51 of the flapper functions to continuously urge the flapper to assume the normal position or arcuate shape depicted in FIG. 3.

Whereas the disclosure of U.S. Pat. No. 3,952,335 contemplated that the flapper 50 be custom-fitted to the particular patient so that such patient could inhale and exhale at comfortable inspiration and expiration pressures, it has been found that it is highly desirable to afford the capability of adjusting the operation of the flapper to accommodate different breathing levels of a particular patient. Thus, for example, when a patient is exercising or is otherwise engaged in a strenuous activity, he will inhale and exhale at pressures significantly above his normal breathing levels. Accordingly, it is felt desirable to afford the capability of adjusting the operational characteristics of the control valve.

To this end, the inventive improvement broadly comprises adjustment means, generally indicated at 53, mounted on the housing and adapted to engage flapper 50 for enabling the normal position of the flapper to be selectively moved further away from the control opening, so that the operational characteristics of the control valve may be selectively varied.

In the preferred embodiment herein illustrated and described, the adjusting means 53 may simply comprise a thumbscrew 54 having a head portion 55 arranged on the outside of the control valve, and having its threaded shank portion 56 matingly received in a horizontal hole 58 provided through the housing end cap 11 between surfaces 16 and 19, so that its right end portion will engage the flapper. Thus, the thumbscrew 54 may be suitably rotated to cause the normal position of the flapper to move further away from the control opening 48, this displaced position being shown in FIG. 4. The effect of rotating the thumbscrew is to change the angle of the flapper with respect to the flow path through the control valve. In the preferred embodiment, the thumbscrew head portion 55 is triangular in shape (FIGS. 1 and 2) so that a wearer may easily count the number of turns of rotation. However, persons skilled in this art will appreciate that the thumbscrew head portion may have other shapes as well. Also, the right end portion of the thumbscrew may be provided with a small head 59 to prevent the thumbscrew from unintentionally separating from the housing.

Therefore, when the wearer exercises and begins to breathe more heavily, he need only rotate the thumbscrew to move the flapper further away from the control opening to vary the operational characteristics of the control valve and accommodate such heavier breathing.

Second Preferred Embodiment (FIGS. 5-10)

Referring collectively to FIGS. 5-10, an improved control valve, generally indicated at 60, is shown as including a housing having a leftward body portion 61, an intermediate end cap portion 62, and a rightward tube portion 63 adapted to be inserted directly into the patient's trachea, or into a "Jackson tube" or a "Shiley tube" inserted into the trachea.

Referring now principally to FIG. 6, the housing body portion 61 is shown as having an annular vertical left end face 64; an annular vertical right end face 65; an inner surface including, from left to right in FIG. 6, a rightwardly convergent frusto-conical inclined surface 66 extending rightwardly from left face 65, a horizontal cylindrical surface 68, a rightwardly divergent frusto-conical seat surface 69, an annular vertical surface 70, a horizontal cylindrical surface 71, a rightwardly facing inclined annular surface 72, and a horizontal cylindrical surface 73 joining the right end face 65; and an outer surface including, from left to right in FIG. 6, a horizontal cylindrical surface 74 extending rightwardly from left end face 64, a leftwardly facing annular vertical surface 75, and a rightwardly convergent frusto-conical surface 76 continuing rightwardly to join right end face 65.

The housing cap portion 62 is shown as having an annular vertical left end face 78; an annular vertical right end face 79; an outer horizontal cylindrical surface 80; and an inner surface including, from left to right in FIG. 6, a horizontal cylindrical surface 81 extending rightwardly from left end face 78, a rightwardly facing annular vertical surface 82, a rightwardly convergent frusto-conical surface 83, an annular vertical surface 84, and a horizontal cylindrical surface 85 continuing rightwardly to join right end face 79. Thus, the housing cap portion 63 is provided with an inwardly facing groove to receive the complementary inwardly directed lug formed on the right marginal end portion of the body portion 61, to hold these members together.

The tube portion 63 is shown as being an arcuate tube member, having a circular cross-section, and provided with a pair of spaced collars, severally indicated at 86, by which the tube portion may be rotatably mounted on the housing cap portion.

An insert, generally indicated at 88, is adapted to be retained within the housing body portion 61 against inclined surface 72. This insert 88 is shown as having an inclined planar left face 89 adapted to abut body portion surface 72; an inclined planar right face 90; an outer surface 91 arranged to face body portion cylindrical surface 73; and an inner surface including, from left to right in FIG. 6, a downwardly and rightwardly convergent frusto-conical seat surface 92, a cylindrical surface 93 continuing downwardly therefrom and a downwardly and rightwardly divergent frusto-conical inclined surface 94 continuing to join right face 90. This insert 88 may be secured in body portion 61 by application of a suitable cement or bonding material 97.

As with the first preferred embodiment, a flapper, generally indicated at 95, is mounted on the housing in the chamber 96 defined therewithin for movement toward and away from each of seat surfaces 69 and 92. This flapper also has a spring portion 98 and a flexible peripheral marginal portion 99.

Therefore, control valve 60 is adapted to be used by a tracheotomy patient provided with a tracheal fistula (not shown) to require the patient to breathe normally through his mouth, but to enable the patient to breathe heavily through his tracheal fistula. The control valve 60 comprises a housing defining chamber 96 therewithin. This housing is provided with a first control opening, generally indicated at 100, communicating chamber 96 with ambient atmosphere, and is provided with a second control opening, generally indicated at 101, adapted to communicate chamber 96 with the patient's tracheal fistula through tube portion 63. A marginal portion of the housing about each of control openings 100, 101 defines a seat 69, 92, respectively, facing the other of the control openings. The control valve 60 further comprises a flapper 95 mounted on the housing in chamber 96 for movement between the first and second control openings 100, 101, and having a flexible peripheral marginal portion 99.

The four modes of operation (i.e., exhalation, coughing, inhalation, and gasping) are depicted in FIGS. 7-10.

Initially, it should be remembered that the flapper 95 has an arcuate shape which is continuously urged to assume the normal unbiased position shown in FIG. 6.

Thereafter, if the patient normally exhales, the flapper 95 will move toward and sealingly assume the contour of the first seat 69 about the first control opening 100 to close the first control opening (FIG. 7). Hence, the patient will be forced to exhale normally through his mouth or nose.

However, should the patient cough (FIG. 8), the flapper 95 is adapted to pass through the first control opening 100, by deformation of flapper marginal portion 99, to permit such cough to be vented through the tracheal fistula. After the cough has occurred, the inclined surface 66 facilitates reinsertion of the flapper 95 into the housing chamber 96.

When the patient normally inhales (FIG. 9), the flapper 95 will move toward and sealingly assume the contour of the second seat 92 about the second control opening 101 to close this second control opening. Hence, the patient will be forced to inhale normally through his mouth or nose.

Finally, if the patient should gasp for air (FIG. 10), the flapper 95 is adapted to pass through the second control opening 101, by deformation of the flapper marginal portion 99, to admit air through the control valve and the patient's tracheal fistula. After the gasp is completed, the inclined surface 94 about the second control opening facilitates reinsertion of the flapper 95 into the housing chamber 96.

Therefore, the inventive control valve 60 is particularly adapted for use by a tracheotomy patient, and functions to require the patient to inhale and exhale normally through his mouth and nose, but to permit the patient to cough and gasp for air through the control valve and the patient's tracheal fistula.

In the embodiments herein illustrated and described, the various parts and components are preferably formed of a suitable acrylic plastic material, or equivalent, and the flapper may be formed of silicone. Desirably, any metal parts or components, such as the pins used to hold the flapper in the control valves, are formed of stainless steel, or equivalent.

Accordingly, while preferred embodiments of the present invention have been shown and described, persons skilled in this art will readily appreciate that various changes and modifications may be made without departing from the spirit of the invention, which is defined in the following claims.

What is claimed is:

1. A control valve for a tracheotomy patient provided with a tracheal fistula and adapted to require said patient to breathe normally through his mouth, but adapted to enable said patient to breathe heavily through said tracheal fistula, comprising:

a housing defining a chamber therewithin, said housing provided with a first control opening communicating said chamber with ambient atmosphere and provided with a second control opening adapted to communicate said chamber with said tracheal fistula, a marginal portion of said housing about each of said control openings defining a seat facing the other of said control openings; and a flapper mounted on said housing in said chamber for movement between said control openings and having a flexible peripheral marginal portion, said flapper being adapted to move toward and sealingly assume the contour of the seat about said first control opening to close said first control opening when said patient normally exhales, said flapper also being adapted to move toward and sealingly assume the contour of the seat about said second control opening to close said second control opening when said patient normally inhales;

whereby said patient may be forced to breathe normally through his mouth but may breathe heavily through said tracheal fistula.

2. The control valve as set forth in claim 1 wherein said flapper is adapted to pass through said first control opening by deformation of said flapper marginal portion should said patient cough.

3. The control valve as set forth in claim 1 wherein said flapper is adapted to pass through said second control opening by deformation of said flapper marginal portional should said patient gasp for air.

* * * * *